United States Patent [19]

Fang et al.

[11] Patent Number: 5,394,735
[45] Date of Patent: Mar. 7, 1995

[54] GAS SENSOR

[75] Inventors: Yen-Kun Fang; Bao-Chsun Fang; Jiann-Ruey Chen; Fu-Yuan Chen, all of Tainan, Taiwan, Prov. of China

[73] Assignee: National Science Council, Taipei, Taiwan, Prov. of China

[21] Appl. No.: 147,841

[22] Filed: Dec. 20, 1993

[51] Int. Cl.$^6$ ............................................. G01N 27/12
[52] U.S. Cl. .................................... 73/31.06; 422/98; 338/34
[58] Field of Search ................. 73/31.06, 31.05; 422/98; 338/34

[56] References Cited

U.S. PATENT DOCUMENTS 4,058,368 11/1977 Svensson et al. .................. 73/31.06
4,224,280 9/1980 Takahama et al. ................ 73/31.06
4,931,851 6/1990 Sibbald .............................. 73/31.06

OTHER PUBLICATIONS

Kawamura, K. et al., "Hydrogen-Sensitive Silicon Tunnel MIS Switching Diodes" IEEE Electron Device Letters, vol. EDL-4 No. 4 Apr. 1983, p. 88.

Primary Examiner—Hezron E. Williams
Assistant Examiner—Michael J. Brock
Attorney, Agent, or Firm—W. Wayne Lianh

[57] ABSTRACT

A gas sensor having a large operation current and being operated at a relatively low temperature includes a substrate having a first surface and a second surface. A sensing area is provided on the first surface for increasing the conductivity across it when the sensing area detects a certain gas. A controlling area is provided on the first surface and beside the sensing area for permitting a tunneling current to pass therethrough when the sensing area cannot sense a certain gas or when the gas sensor is adapted to be sufficiently supplied with power. This control area prevents the tunneling current from being generated when the sensing area detects certain gas and thus the conductivity is increased, so that when the first and the second surfaces are electrically connected to the power supply. The gas sensor will be in an on state when the gas sensor cannot sense there is the certain gas and be in an off state when the gas sensor detects the presence of certain gas. This gas sensor can avoid a dangerous explosion resulting from a flammable gas at a relatively high temperature. The gas sensor possesses a relatively short response time.

18 Claims, 3 Drawing Sheets

GAS SENSOR

BACKGROUND OF THE INVENTION

The present invention relates generally to a gas sensor and more particularly to a gas sensor operated at room temperature.

One conventional technique for the gas sensor utilizes the MIS (metal insulator semiconductor) switch diode structure. K. Kawamura and T. Yamamoto have prepared the MIS switch diode as a high sensitivity hydrogen gas sensor with catalytic metal Pd as the cathode electrode (i.e., with a Pd/SiO$_2$/n (Si)/p+(Si) structure). Due to a slow catalytic reaction under low temperature, the catalytic MIS sensor has a poor response time and poor sensitivity during room-temperature operation. Thus it is better to be used at an elevated temperature, i.e., above 100° C. The catalytic MIS sensor under high temperature operation, however may be hazardous upon contact with a flammable gas such as hydrogen or ethanol. Furthermore, this catalytic MIS sensor is only sensitive to hydrogen.

As shown in FIG. 1, the structure of the conventional resistive gas sensor includes an SnO$_2$ layer 2, an epitaxial silicon substrate 1, a palladium electrode 3, and an aluminum electrode 4. Because under an elevated temperature, palladium is an excellent catalytic metal, and also because the conducting electrons resulting from the surface defect of the SnO$_2$ layer Z play an important role in sensing some poisonous or flammable gas, the palladium electrodes 3 can permit the poisonous or flammable gas to be absorbed by the SnO$_2$ layer 2 whose conductivity will thus be changed. This absorption can in turn be used to locate the existence and the amount of the poisonous or flammable gas. Due to consideration of the sensitivity of the conductivity of SnO$_2$ layer 2 in which the sensitivity $S=(G-G_0)/(G_0)$. In this case Go represents a conductivity of SnO$_2$ layer 2 in air. Therefore G, a conductivity of SnO$_2$ layer 2 can absorb the poisonous or flammable gas. The resistance of SnO$_2$ layer 2 is to be relatively high (in kilo ohm order). With this in mind, the operation current of the gas sensor is too small to drive an alarm or a security system.

The conventional resistive gas sensor in summary has the following disadvantages:

1) Because the resistance of SnO$_2$ layer 2 is relatively high, the sensitivity thereof cannot meet demand and its gas sensing effect is not satisfactory.

2) Because palladium electrode 3 operates only under a relatively high temperature (e.g., over 100° C.), it is very dangerous when the gas to be sensed is flammable.

3) Because the operation current is relatively small, an amplifying system is a must and the cost is therefore relatively higher.

4) The catalytic gas sensor has a poor response time. There is a time delay that occurs in the interval after the gas sensor detects the poisonous or flammable gas and before the alarm system sounds, which is normally hazardous.

It is therefore left to the applicant to deal with this unsatisfactory situation described above.

SUMMARY OF THE INVENTION

An object of the present invention is to provide a gas sensor for operation at room temperature.

A further object of the present invention is to provide a gas sensor which prevents dangerous explosions resulting from ignition of flammable gases at relatively high temperatures.

Another object of the present invention is to provide a gas sensor which uses a relatively high operation current.

Still another object of the present invention is to provide a gas sensor which operates on a relatively short response time.

Another object of the present invention is to provide a gas sensor with a relatively high sensitivity to both hydrogen and ethanol.

Still another object of the present invention is to provide a gas sensor whose operation current need not be amplified in order to run an alarm or a security system.

Another object envisaged for the present invention is to provide a low cost gas sensor.

In accordance with the present invention, a gas sensor with a large operation current operated at a relatively low temperature basically comprises a substrate having a first surface and a second surface. A sensing area is on the first surface to increase surface conductivity. When the sensing area detects a certain gas, a control area provided on the first surface comes into operation. This control area on the first surface beside the sensing area permits a tunneling current to pass therethrough when the sensing area cannot detect a certain gas or when the gas sensor is adapted to be sufficiently power-supplied by a power supply. This sensing area prevents the tunneling current from being generated when the sensing area picks up the presence of certain gas and thus the conductivity is increased. When the first and the second surfaces are electrically connected to the power supply, the gas sensor will be in an on state. If the gas sensor cannot detect certain gas and switches off in the presence of certain gas.

Preferably the present gas sensor also includes a cathode electrically connected to the controlling area and the sensing area and an anode connected to the second surface.

Certainly, the substrate can be an n/p+ epitaxial silicon substrate. The first surface can be an upper surface of the n/p+ epitaxial silicon substrate. The second surface can be a lower surface of the n/p+ epitaxial silicon substrate.

The sensing area can include an SnO$_2$ layer. The SnO$_2$ layer can have a thickness ranging from about 600 Å to about 800 Å. The SnO$_2$ layer can be obtained by electron gun evaporating.

The cathode can be made of argentum or aurum, obtained by evaporating.

The sensing area can be in parallel with the controlling area for permitting the tunneling current to pass through the controlling area when the conductivity of the sensing area does not increase.

The sensing area can be in parallel with the controlling area to permit a major portion of a current from the power supply to pass through the sensing area. A minor portion of the current from the power supply will pass through the controlling area when the conductivity of the sensing area is increased. The minor portion of the current can be diverted to establish a relatively small terminal voltage across the control area so as not to permit the generation tunneling current.

The anode can be made of aluminum and obtained by evaporating.

The controlling area can include an insulating layer. The insulating layer can be an SiO$_2$ layer. The SiO$_2$ layer can have a thickness ranging from about 25 Å to about 35 Å.

The certain gas can be hydrogen or ethanol.

Additionally, the gas sensor can include a power supply of 2V DC to run itself.

The present invention can be more fully understood in reference to the following description and accompanying drawings, which form an integral part of this application.

DETAILED DESCRIPTION OF THE PREFERRED EMBODIMENT

Figure 1:
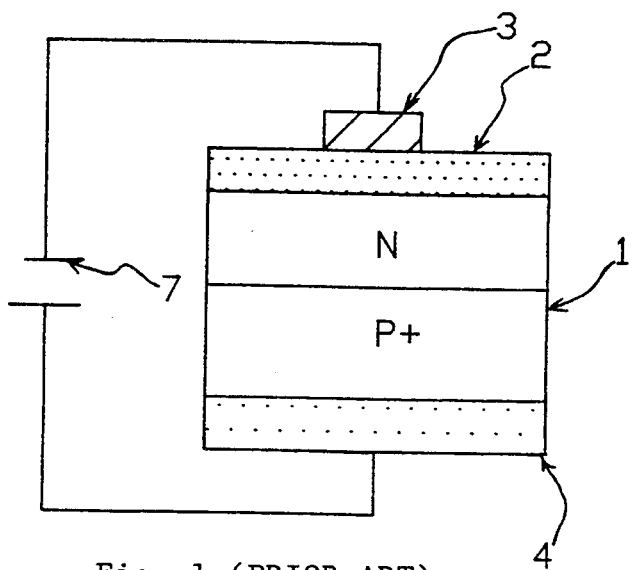
FIG. 1 schematically shows a conventional resistive gas sensor.
Figure 2:
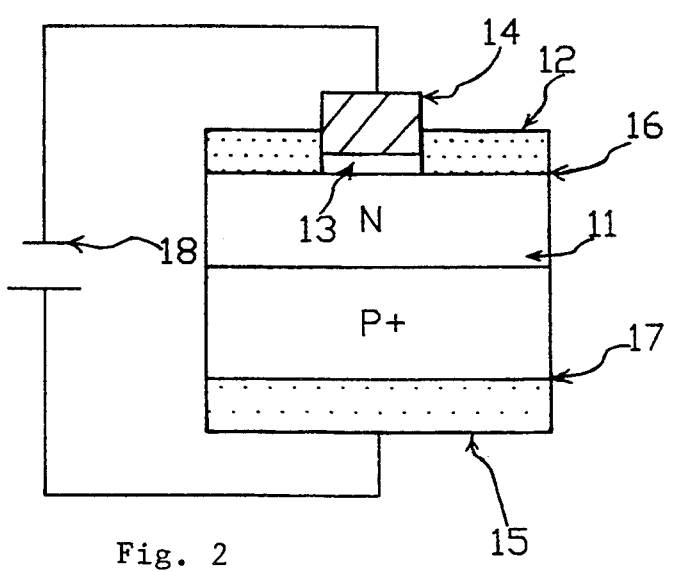
FIG. 2 shows a gas sensor, with high operation current, operated at room temperature, according to the present invention.

Referring to FIG. 2, a preferred embodiment of the present gas sensor includes an n/p+ epitaxial silicon substrate 11 having a first surface 16 being an upper surface of the substrate 11 and a second surface 17 being a lower surface of the substrate 11. FIG. 2 also shows a sensing area 12 made of an $SnO_2$ layer, a controlling area 13 of an $SiO_2$ layer. Cathode 14 made of argentum or aurum and connects to the $SnO_2$ layer 12 and the $SiO_2$ layer 13. Anode 15 made of aluminum and connects to the second surface 17. It is to be noticed that the $SnO_2$ layer 12 and $SiO_2$ layer 13 are in parallel. The power supply 18 sufficiently supplies the present gas sensor with about 2 volts. When the present gas sensor cannot sense a certain gas, $SiO_2$ layer 13 permits a tunneling current to pass therethrough to put the gas sensor in an on state. When the gas sensor senses there is a certain gas, the conductivity of $SnO_2$ layer 12 is increased and thus $SnO_2$ layer 12 can draw a major portion of a current from the power supply 18. Since a minor portion of the current from power supply 18 is too small to establish a terminal voltage across SiO2 layer 13, the tunneling current is prevented from being generated. Then the gas sensor is in an off state.

It is also to be noticed that $SnO_2$ layer 12 can have a thickness from about 600 Å to about 800 Å and $SiO_2$ layer 13 has a thickness from about 25 Å to about 35 Å. The thickness of $SiO_2$ layer 13 is to be properly controlled. If it is too thick, the gas sensor cannot conduct; and if it is too thin, the gas sensor becomes a p-n diode. Besides, $SnO_2$ layer 12 can be obtained by electron gun evaporating, and the cathode 14 and the anode 15 can be obtained by evaporating. The gases sensible to the present gas sensor include, hydrogen and ethanol.

Figure 4:
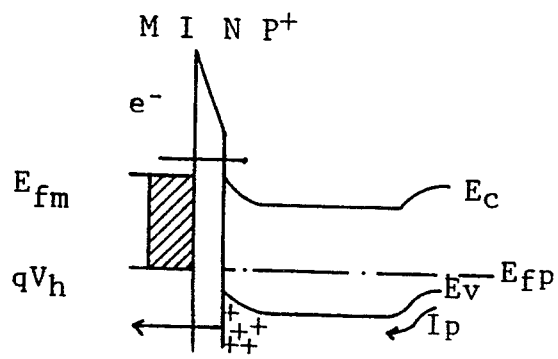
FIG. 4 shows that the voltage applied to a gas sensor of the present invention mainly drops at the $SiO_2$ layer.
Figure 5:
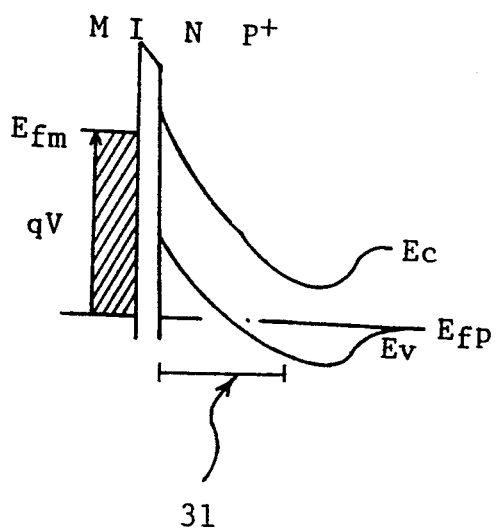
FIG. 5 shows that a depletion region exists in the n layer under the $SiO_2$ layer of the present invention. It also shows that the gas sensor according to the present invention switches back to an off state in reaction to a lack of a large tunneling current through the $SiO_2$ layer and a diffusion current in the n/p+ junction.

The voltage applied to the present gas sensor in an on state mainly drops at $SiO_2$ layer 13 as shown in FIG. 4, making the tunneling current through $SiO_2$ layer 13 high enough to hold the present gas sensor in an on state. However, if the present gas sensor, once turned on, is put into a reducing gas (e.g., $H_2$ or $C_2H_5oH$) atmosphere, the resistance of $SnO_2$ layer 12 decreases with an increasing gas concentration. Ultimately, the $SnO_2$ layer 12 becomes a parallel conductor to $SiO_2$ layer 13. Once $SnO_2$ layer 12 becomes conductive, the voltage drop across $SiO_2$ layer 13 reduces and is no longer high enough for the generation of a large electron tunneling current. Thus, a depletion region 31 exists in the n layer under $SiO_2$ layer 13 as shown in FIG. 5. At this time, the applied bias drops at the existing depletion region. At this point the gas sensor switches back to the off state due to the lack of a large tunneling current through $SiO_2$ layer 13 and a diffusion current in the n/p+ junction.

The present gas sensor utilizes $SnO_2$ as the gas-sensing material, especially sensitive to hydrogen and ethanol, and applies the MIS switch structure. Therefore, owing to the increased sensitivity, the response time is shortened. The operating temperature can be room temperature. The present gas sensor can directly drive an alarm or security system because it uses the MIS switch structure.

The production procedures of the present gas sensor include:

A) flushing n/p+ silicon substrate 11.

B) growing $SiO_2$ layer 13 with a thickness ranging from about 25 Å to about 35 Å on upper surface 16 and lower surface 17 of substrate 11 in dry oxygen at 700° C.

C) evaporating a 5000 Å Ag layer on $SiO_2$ layer 13, through a metal mask at $1 \times 10^{-5}$ torr, to be cathode 14.

D) coating a positive photoresist on cathode 14 and drying substrate 11.

E) dipping substrate 11 in a solution consisting of HF and $H_2O$ whose ratio is 1 to 10, and flushing it with DI water.

F) growing $SnO_2$ layer 12 on upper surface 16 by evaporation with an electron gun.

G) dipping substrate 11 in acetone (ACE) and applying a lift-off technique to remove the positive photoresist and $SnO_2$ layer 12 mounted on the positive photoresist.

H) annealing substrate 11 at about 700° C. for 2 hours; and

I) removing $SiO_2$ layer 13 mounted on lower surface 17 and forming an Al layer on lower surface 17 that forms anode 15.

Figure 3:
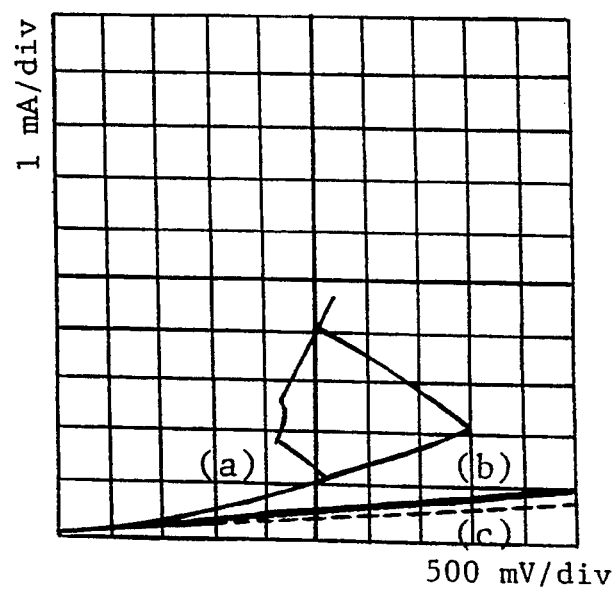
FIG. 3 shows turn-on and turn-off I–V curves of the present gas sensor respectively in air atmosphere (a), 200 ppm ethanol gas atmosphere (b), and 250 ppm hydrogen gas atmosphere (c) according to the present invention.

FIG. 3 shows the on-of I–V curves in an air atmosphere (a), 200 ppm ethanol gas atmosphere (b), and 250 ppm hydrogen gas atmosphere (c), respectively. The impact of these gases on the maximum controllable current $I_{ak}$, i.e., the gate turn-off capability is listed in TABLE 1. The gate turn-off capability was measured by connecting the sensor in a testing chamber in series with an adjustable load to modulate the sensor current. The load signal is then displayed in a curve tracer. The table shows that gate turn-off capability is proportional to the detected gas concentration.

Note that the same circuit can be used to measure the gate turn-off response time. The response time is measured as the time required for the signal wave amplitude to attenuate from 100% to 10%. Table 2 lists the attenuation times (with the sensor current $I_{ak}$ set at 1 mA) of the signal wave amplitude in the gas sensor at room temperature in an ethanol or hydrogen gas atmosphere. The results show that the sensor has a shorter response time for detecting ethanol gas than for hydrogen gas detection under the same ppm concentration, since the ethanol gas has a larger gate turn-off capability. However, both measurements show that the present gas sensor with the operation current at tens of mA can be turned off by only a few hundred ppm ethanol gas or hydrogen gas within 10 seconds under room temperature. Thus the device can be used as a quick response, high sensitivity gas sensor.

In summary, the use of an E-gun to prepare $SnO_2$ layer 12 as a sensing material provides high sensitivity for the gas sensor. The use of an MIS switch structure with high speed turn-off ability offers the quick response time for the gas sensor. So the present gas sensor can detect ethanol gas and hydrogen gas quickly with high sensitivity under room temperature.

While the present invention has been described in what is considered to be the most practical and preferred embodiment, it is to be understood that the invention is not to be limited to the disclosed embodiment. This invention is intended to cover various modifications and equivalent arrangements included within the spirit and scope of the appended claims whose scope is to be accorded the broadest interpretation to include all modifications and equivalent structures.

What is claimed is:

1. A gas sensor to be powered by a power supply comprising:
    a substrate having a first surface and a second surface;
    a sensing area provided on said first surface and in serial relationship with said first surface, said sensing area having a variable conductivity which will increase when said sensing area senses the presence of a certain gas; and
    a controlling area provided on said first surface, said controlling area being in serial relationship with said first surface and in parallel relationship with said sensing area said controlling area being adapted to allow a tunneling current to pass therethrough when said sensing area does not detect the presence of said certain gas and when said gas sensor is sufficiently power-supplied by the power supply, said controlling area being further adapted to prevent said tunneling current from passing therethrough when said sensing area senses the presence of said certain gas and thus said conductivity of said sensing area is increased, whereby when said first and said second surfaces are electrically connected to the power supply, said gas sensor will be in a turned-on state when said gas sensor does not detect the presence of said certain gas, and will be in a turned-off state when said gas sensor detects the presence of said certain gas.

2. A gas sensor according to claim 1 wherein said substrate is an n/p+ epitaxial silicon substrate.

3. A gas sensor according to claim 2 wherein said n/p+ epitaxial silicon substrate containing an n-layer deposited on a p+-layer, and said first surface is an outer surface of said n/p+ epitaxial silicon substrate.

4. A gas sensor according to claim 2 wherein said n/p+ epitaxial silicon substrate containing an n-layer deposited on a p+-layer, and said second surface is an inner surface of said n/p+ epitaxial silicon substrate.

5. A gas sensor according to claim 1 wherein said sensing area includes a $SnO_2$ layer.

6. A gas sensor according to claim 5 wherein said $SnO_2$ layer has a thickness ranging from about 600 Å to about 800 Å.

7. A gas sensor according to claim 1 wherein said sensing area is in parallel with said controlling area for permitting a major portion of a current from said power supply to pass through said sensing area, and a minor portion of said current from said power supply to pass through said controlling area when said conductivity of said sensing area is increased.

8. A gas sensor according to claim 7 wherein said minor portion of said current establishes a relatively small terminal voltage being across said controlling area and being unable to permit said tunneling current to be generated.

9. A gas sensor according to claim 1 wherein said anode is made of aluminum.

10. A gas sensor according to claim 1 wherein said controlling area includes an insulating layer.

11. A gas sensor according to claim 10 wherein said insulating layer is an $SiO_2$ layer.

12. A gas sensor according to claim 11 wherein said $SiO_2$ layer has a thickness ranging from about 25 Å to about 35 Å.

13. A gas sensor according to claim 1 wherein said certain gas is hydrogen.

14. A gas sensor according to claim 1 wherein said certain gas is ethanol.

15. A gas sensor according to claim 1, which further comprising a power supply for supplying power to said gas sensor.

16. A gas sensor according to claim 15 wherein said gas power supply supplies 2V DC.

17. A gas sensor according to claim 1, further comprising a cathode electrically connected to said controlling area and said sensing area; and
    an anode electrically connected to said second surface.

18. A gas sensor according to claim 1 wherein said cathode is made of argentum or aurum.

* * * * *